US005871986A

United States Patent [19]
Boyce

[11] Patent Number: 5,871,986
[45] Date of Patent: *Feb. 16, 1999

[54] USE OF A BACULOVIRUS TO EXPRESS AND EXOGENOUS GENE IN A MAMMALIAN CELL

[75] Inventor: Frederick M. Boyce, Belmunt, Mass.

[73] Assignee: The General Hospital Corporation, Boston, Mass.

[ * ] Notice: The term of this patent shall not extend beyond the expiration date of Pat. No. 5,731,182.

[21] Appl. No.: 311,157

[22] Filed: Sep. 23, 1994

[51] Int. Cl.$^6$ .............................. C12N 9/00; C12N 15/63; C12N 5/10; C07H 21/04
[52] U.S. Cl. ........................ 435/183; 435/320.1; 435/325; 536/23.2
[58] Field of Search ................................. 435/183, 320.1, 435/240.2, 70.1, 70.3; 536/23.2

[56] References Cited

U.S. PATENT DOCUMENTS

| | | | |
|---|---|---|---|
| 4,745,051 | 5/1988 | Smith et al. | 435/68 |
| 4,879,236 | 11/1989 | Smith et al. | 435/235 |
| 4,914,027 | 4/1990 | Knapp et al. | 435/69.6 |
| 5,004,687 | 4/1991 | Miller | 435/69.1 |
| 5,106,741 | 4/1992 | Marotti et al. | 435/226 |

FOREIGN PATENT DOCUMENTS

WO 95/23866  9/1995  WIPO .

OTHER PUBLICATIONS

Glocker, B. et al. (1992) "In vitro transactivation of baculovirus early genes by nuclear extracts from Autographa californica nuclear polyhedrosis virus–infected *Spodoptera frugiperda* cells" J. Virol. 66(6):3476–3484, Jun. 1962.

Boyce, F.M. et al. (1996) "Baculovirus–mediated gene transfer into mammalian cells" Proc. Nat'l. Acad. Sci., USA 93:2348–2352, Nov. 1996.

Fraser, M.J. (1992) "The baculovirus–infected insect cell as a eukaryotic gene expression system" Curr. Top. Microobiol. Immunol. 158:131–172, Aug. 1992.

Trujillo, M.A. et al. (1991) "Functional analysis of a liver––specific enhancer of the hepatitis B virus" Proc. Nat'l. Acad. Sci., USA 88:3797–3801, May 1991.

Ashwell G. et al.; "Carbohydrate–Specific Receptors of the Liver"; Ann. Rev. Biochem. 51:531–54 (1982).

Blissard G.W. et al.; "Baculovirus Diversity and Molecular Biology"; Annu. Rev. Entomol. 35:127–55 (1990).

Blissard G.W. et al.; "Baculovirus gp64 Envelope Glycoprotein Is Sufficient To Mediate pH–Dependent Membrane Fusion"; J. of Virology 66:6829–6835 (1992).

Burhans W.C. et al.; "DNA Replication Origins in Animal Cells:A Question of Context?"; Science 263:639–640 (1994).

Burns J.C. et al.; "Vesicular Stomatitis Virus G Glycoprotein Pseudotyped Retroviral Vectors:Concentration to Very High Titer and Efficient Gene Transfer into . . . "; Proc. Natl. Acad. Sci. USA; 90:8033–8037 (1993).

Carbonell L.F. et al.; "Baculovirus–Mediated Expression of Bacterial Genes in Dipteran and Mammalian Cells" Journal of Virology, 56:153–160 (1985).

Carbonell L.F. et al.; "Baculovirus Interaction with Nontarget Organisms:A Virus–Borne Reporter Gene Is not Expressed in Two Mammalian Cell Lines"; Applied and Environmental Microbiology 53:1412–1417 (1987).

Charreau B. et al; "Establishment of Porcine Cell Lines Producing a Murine Recombinant Retrovirus in order to Transfer the nislacZ Gene into Porcine Cells"; Res. Virol. 142:343–351 (1991).

Cotten M. et al.; "Receptor–Mediated Transport of DNA into Eukaryotic Cells"; Academic Press, Inc. 217:618–644 (1993).

Cristiano R.J. et al.; "Hepatic Gene Therapy:Adenovirus Enhancement of Receptor–Mediated Gene Delivery and Expression in Primary Hepatocytes"; Proc. Natl. Acad. Sci. USA 90:2122–2126 (1993).

Demarquoy J.; "Retroviral–Mediated Gene Therapy for the Treatment of Citrullinemia. Transfer and Expression of Argininosuccinate Synthetase in Human Hematopoietic Cells"; Experientia 49:345–348 (1993).

Demetrio A.A. et al.; "Replacement of Liver Function in Rats by Transplantation of Microcarrier–Attached Hepatocytes"; Science 233:1190–1192 (1986).

Grompe M. et al.; "Gene Therapy in Man and Mice:Adenosine Deaminase Deficiency, Ornithine Transcarbamylase Deficiency, and Duchenne Muscular Dystrophy"; Adv. in Experimental Medicine & Biology 3098:51–56 (1991).

Grompe M. et al.; "Retroviral–Mediated Gene Transfer of Human Ornithine Transcarbamylase into Primary Hepatocytes of spf and spf–ash Mice"; Human Gene Therapy 3:35–44 (1992).

Groner, et. al; "Interaction of Autographa californica Nuclear Palyhedrosis Virus with Two Nonpermissive Cell Lines"; Intervirology 21:203–209 (1984).

Hartig P.C. et al.; "Insect Virus:Assays for Toxic Effects and Transformation Potential in Mammalian Cells"; Applied and Enviornmental Microbiology 55:1916–1920 (1989).

Hartig P.C. et al.; "Insect Virus:Assays for Viral Replication and Persistence in Mammalian Cells"; J. Virological Methods 31:335–344 (1991).

Hata A. et al.; "Structure of the Human Ornithine Transcarbamylase Gene"; J. Biochem (Tokyo) 103:302–308 (1988).

(List continued on next page.)

Primary Examiner—Kawai Lau
Attorney, Agent, or Firm—Fish & Richardson, P.C.

[57] ABSTRACT

Disclosed is a method of expressing an exogenous gene in a mammalian cell, involving infecting the cell with a baculovirus whose genome carries an exogenous gene, and growing the cell under conditions such that the gene is expressed. Also disclosed is a method of treating a gene deficiency disorder in a mammal by providing to a cell a therapeutically effective amount of a baculovirus whose genome carries an exogenous gene and growing the cell under conditions such that the exogenous gene is expressed in the mammal.

36 Claims, 3 Drawing Sheets

OTHER PUBLICATIONS

Hodges P.E. et al.; "The spf$^{ash}$ Mouse:A Missense Mutation in the Ornithine Transcarbamylase Gene Also Causes Aberrant mRNA Splicing"; *Proc. Natl. Acad. Sci. USA* 86:4142–4146 (1989).

Horwich A.L.; "Inherited Hepatic Enzyme Derfects as Candidates for Liver–Directed Gene Therapy", *Current Topics in Microbiology and Immunology* 168:185–200 (1991).

Jones S.N. et al.; "Ectopic Correction of Ornithine Transcarbamylase Deficiency in Sparce Fur Mice"; *J. Biological Chemistry* 265:14684–14690 (1990).

Jung et al.; "A Novel β–Galactoside–Binding Lectin in Adult Rat Kidney"; *J. Biochem.* 116:547–553 (1994).

Kasahar, et al.; "Tissue–Specific Targeting of Retroviral Vectors Through Ligand–Receptor Interactions"; *Science* 266:1373–1376 (1994).

Lodish H.F.; "Recognition of Complex Oligosaccharides by the Multi–Subunit Asialoglycoprotein Receptor"; *Elsevier Science Publishers* 374–377 (1991).

Maestri N.E. et al.; "Prospective Treatment of Urea Cycle Disorders"; *J. of Pediatrics* 119:923–928 (1991).

McGrane M.M. et al.; "Metabolic Control of Gene Expression:In Vivo Studies With Transgenic Mice"; *Elsevier Science Publishers* 17:40–44 (1992).

Midoux P. et al.; "Specific Gene Transfer Mediated by Lactosylated Poly–L–Lysine into Hepatome Cells"; *Nucleic Acids Research* 21:871–878 (1993).

Mulligan R.C.; "The Basic Science of Gene Therapy"; *Science* 260:926–932 (1993).

Shen R. et al.; "Tissue–Specific Regulation of Human $\alpha_1$–Antitrypsin Gene Expression in Transgenic Mice"; *DNA* 8:101–108 (1989).

Shimada T. et al.; "Correction of Ornithine Transcarbamylase (OTC) Deficiency in spf–ash Mice by Introduction of Rat OTC Gene"; *Elsevier Science Publishers* 279:198–200 (1991).

Spiess, Martin; "The Asialoglycoprotein Receptor: A Model for Endocytic Transport Receptors"; *Biochemistry* 29:10009–10018 (1990).

Stratford–Perricaudet et al.; "Evaluation of the Transfer and Expression in Mice of an Enzyme–Encoding Gene Using a Human Adenovirus Vector"; *Human Gene Therapy* 1:241–256 (1990).

Tan S.; "Liver–Specific and Position–Effect Expression of a Retinol–Binding Protein–LacZ Fusion Gene (RBP–lacZ) in Transgenic Mice"; *Developmental Biology* 146:24–37 (1991).

Volkman, et al.; "In Vitro Survey of Autographa californica Nuclear Polyhedrosis Virus Interaction with Nontarget Vetebrate Host Cells" *Applied and Environmental Microbiology* 45:1085–1093 (1983).

Wagner E. et al.; "Transferrin–Polycation Conjugates as Carriers for DNA Uptake into Cells"; *Proc. Natl. Acad. Sci. USA* 87:3410–3414 (1990).

Wilson J.M. et al.; "A Novel Mechanism for Achieving Transgene Persistence in Vivo After Somatic Gene Transfer into Hepatocytes"; *Journal of Biological Chemistry* 267:11483–11489 (1992).

Wilson J.M. et al.; "Hepatocyte–Directed Gene Transfer In Vivo Leads to Transient Improvement of Hypercholesterolemia in Low Density Lipoprotein . . . "; *J. Biol. Chemistry* 267:963–967 (1992).

Wu G.Y. et al.; "Evidence for Targeted Gene Delivery to Hep G2 Hepatoma Cells in Vitro"; *Biochemistry* 27:887–892 (1988).

Wu G.Y. et al.; "Receptor–Mediated Gene Delivery and Expression in Vivo"; 263:14621–14624 (1988).

Wu G.Y. et al.; "Receptor–Mediated Gene Delivery in Vivo"; *J. Biological Chemistry* 266:14338–14342 (1991).

Wu G.Y. et al.; "Receptor–Mediated in Vitro Gene Transformation by a Soluble DNA Carrier System"; *J. Biological Chemistry* 262:4429–4432 (1987).

Wu G.Y. et al.; "Targeting Genes:Delivery and Persistent Expression of a Foreign Gene Driven by Mammalian Regulatory Elements in Vivo"; *J. Biological Chemistry* 264:16985–16987 (1989).

Young J.A.T. et al.; "Efficient Incorporation of Human CD4 Protein into Avian Leukosis Virus Particles"; *Science* 250:1421–1423 (1990).

USE OF A BACULOVIRUS TO EXPRESS AND EXOGENOUS GENE IN A MAMMALIAN CELL

BACKGROUND OF THE INVENTION

This invention relates to the use of a baculovirus genome to express an exogenous gene in a mammalian cell.

Viruses of the family Baculoviridae (commonly referred to as baculoviruses) have been used to express exogenous genes in insect cells. One of the most studied baculoviruses is the *Autographa californica* multiple nuclear polyhedrosis virus (AcMNPV). Although some species of baculoviruses which infect crustacea have been described (Blissard, et al., 1990, Ann. Rev. Entomology 35: 127), the normal host range of the baculovirus AcMNPV is limited to the order lepidoptera.

Current methods of expressing genes in a mammalian cell include the use of viral vectors, such as those which are derived from retroviruses, adenoviruses, herpes viruses, vaccinia viruses, polio viruses, sindbis viruses, or adeno-associated viruses. Other methods of expressing an exogenous gene in a mammalian cell include direct injection of DNA, the use of ligand-DNA conjugates, the use of adenovirus-ligand-DNA conjugates, calcium phosphate precipitation, and methods which utilize a liposome- or polycation-DNA complex. In some cases, the liposome- or polycation-DNA complex is able to target the exogenous gene to a specific type of tissue, such as liver tissue. Some methods of targeting genes to liver cells utilize the asialoglycoprotein receptor (ASGP-R) which is present on the surface of hepatocytes (Spiess et al., 1990, Biochem. 29: 10009–10018). The ASGP-R is a lectin which has affinity for the terminal galactose residues of glycoproteins. In these cases, the DNA complexes are endocytosed by the cell after they are bound to the ASGP-R on the cell surface.

Gene therapy methods are currently being investigated for their ability to correct inborn errors of the urea cycle (see, e.g., Wilson et al., 1992, J. Biol. Chem. 267: 11483–11489). The urea cycle is the predominant metabolic pathway by which nitrogen wastes are eliminated from the body. The steps of the urea cycle are primarily limited to the liver, with the first two steps occurring within hepatic mitochondria. In the first step, carbamoyl phosphate is synthesized in a reaction which is catalyzed by carbamoyl phosphate synthetase I (CPS-I). In the second step, citrulline in formed in a reaction catalyzed by ornithine transcarbamylase (OTC). Citrulline then is transported to the cytoplasm and condensed with aspartate into arginosuccinate by arginosuccinate synthetase (AS). In the next step, arginosuccinate lyase (ASL) cleaves arginosuccinate to produce arginine and fumarate. In the last step of the cycle, arginase converts arginine into ornithine and urea.

A deficiency in any of the five enzymes involved in the urea cycle has significant pathological effects, such as lethargy, poor feeding, mental retardation, coma, or death within the neonatal period (see, e.g., Emery et al., 1990, In: Principles and Practice of Medical Genetics, Churchill Livingstone, New York). OTC deficiency usually manifests as a lethal hyperammonemic coma within the neonatal period. A deficiency in AS results in citrullinemia which is characterized by high levels of citrulline in the blood. The absence of ASL results in arginosuccinic aciduria (ASA), which results in a variety of conditions including severe neonatal hyperammonemia and mild mental retardation. An absence of arginase results in hyperargininemia which can manifest as progressive spasticity and mental retardation during early childhood.

Current therapies for hepatic disorders include dietary restrictions, liver transplantation, and administration of arginine freebase, sodium benzoate, and/or sodium phenylacetate.

SUMMARY OF THE INVENTION

I have discovered that an AcMNPV carrying an exogenous gene expression construct can target expression of the exogenous gene to the HepG2 liver cell line.

Accordingly, in one aspect, the invention features a method of expressing an exogenous gene in a mammalian cell, involving introducing into the cell a baculovirus (also referred to herein as a "virion") whose genome carries the exogenous gene, and allowing the cell to live or grow under conditions such that the exogenous gene is expressed.

Preferably, the baculovirus is a nuclear polyhedrosis virus; more preferably, the virus is AcMNPV. The baculovirus genome can carry an exogenous promoter positioned for expression of the exogenous gene. Preferred promoters include the long terminal repeat (LTR) promoters of retroviruses such as Rous Sarcoma Virus (RSV). Other preferred promoters include the LTRs of transposable elements and mammalian promoters, including cell-type-specific promoters. The baculoviral genome can also carry a polyadenylation signal and an RNA splicing signal positioned for proper processing of the product of the exogenous gene. In various embodiments, the mammal is a human, and the cell is a hepatocyte or a cell having an ASGP-R.

In another aspect, the invention is used to treat a gene deficiency disorder in a mammal. The method involves introducing into a cell a therapeutically effective amount of a baculovirus whose genome carries an exogenous gene, and allowing the cell to live or grow in the mammal under conditions such that the exogenous gene is expressed.

Preferably, the baculovirus is a nuclear polyhedrosis virus; more preferably, the virus is AcMNPV. In various embodiments, the mammal is a human, the cell is a hepatocyte, and the cell has an ASGP-R. The baculovirus can by introduced into a cell by administering the baculovirus to a mammal having the cell. In other embodiments, the baculovirus is introduced into the cell in vitro, and the cell is then introduced into the mammal (e.g., by intraperitoneal injection). Thus, for expression of the exogenous gene, the cell can be allowed to live or grow in vivo or in vitro and in vivo, sequentially.

Appropriate genes for expression in the cell include, without limitation, those genes which are expressed in normal cells of the type of cell to be infected, but expressed at less than normal levels in the particular cell to be infected, and those genes which are not normally expressed in a cell of the type to be infected.

In various embodiments of either aspect of the invention, the gene encodes carbamoyl synthetase I, ornithine transcarbamylase, arginosuccinate synthetase, arginosuccinate lyase, arginase fumarylacetoacetate hydrolase, phenylalanine hydroxylase, alpha-1 antitrypsin, glucose-6-phosphatase, low-density-lipoprotein receptor, porphobilinogen deaminase, carbamoyl synthetase I, ornithine transcarbamylase, arginosuccinate synthetase, arginosuccinate lyase, arginase, factors VIII or IX, cystathione β-synthase, branched chain ketoacid decarboxylase, albumin, isovaleryl-CoA dehydrogenase, propionyl CoA carboxylase, methyl malonyl CoA mutase, glutaryl CoA dehydrogenase, insulin, β-glucosidase, pyruvate carboxylase, hepatic phosphorylase, phosphorylase kinase, glycine decarboxylase (also referred to as P-protein), H-protein, T-protein, Menkes disease protein, or the product of Wilson's disease gene pWD.

By "positioned for expression" is meant that the DNA molecule which includes the exogenous gene is positioned adjacent a DNA sequence which directs transcription and, if desired, translation of the DNA and RNA (i.e., facilitates the production of the exogenous gene product or an RNA molecule).

By "promoter" is meant minimal sequence sufficient to direct transcription. Also useful in the invention are those promoters which are sufficient to render promoter-dependent gene expression controllable for cell-type specificity, cell-stage specificity, or tissue-specificity (e.g., liver-specific promoters), and those promoters which are inducible by external signals or agents; such elements can be located in the 5' or 3' regions of the native gene.

By "operably linked" is meant that a gene and a regulatory sequence(s) (e.g., a promoter) are connected in such a way as to permit gene expression when the appropriate molecules (e.g., transcriptional activator proteins) are bound to the regulatory sequence(s).

By "exogenous" gene or promoter is meant any gene or promoter which is not normally part of the baculovirus genome. Such genes include those genes which normally are present in the mammalian cell to be infected; also included are genes which are not normally present in the mammalian cell to be infected (e.g., related and unrelated genes of other cells and of other species).

The invention is useful for expressing an exogenous gene(s) in a mammalian cell (e.g., a cultured hepatocyte such as HepG2). This method can be employed in the manufacture of useful proteins, such as proteins which are used pharmaceutically. The method can also be used therapeutically. For example, the invention can be used to express in a patient a gene encoding a protein which corrects a deficiency in gene expression.

A baculoviral expression system offers the following advantages: (1) baculoviruses are not normally pathogenic to humans; (2) the viruses can be propagated in serum-free media and grown to a titer of over $10^8$ pfu/ml; and (3) the genome of the virus accepts large exogenous DNA molecules.

Other features and advantages of the invention will be apparent from the following description of the preferred embodiments thereof, and from the claims.

DETAILED DESCRIPTION

The drawings will first be described.

Drawings

Figure 1:
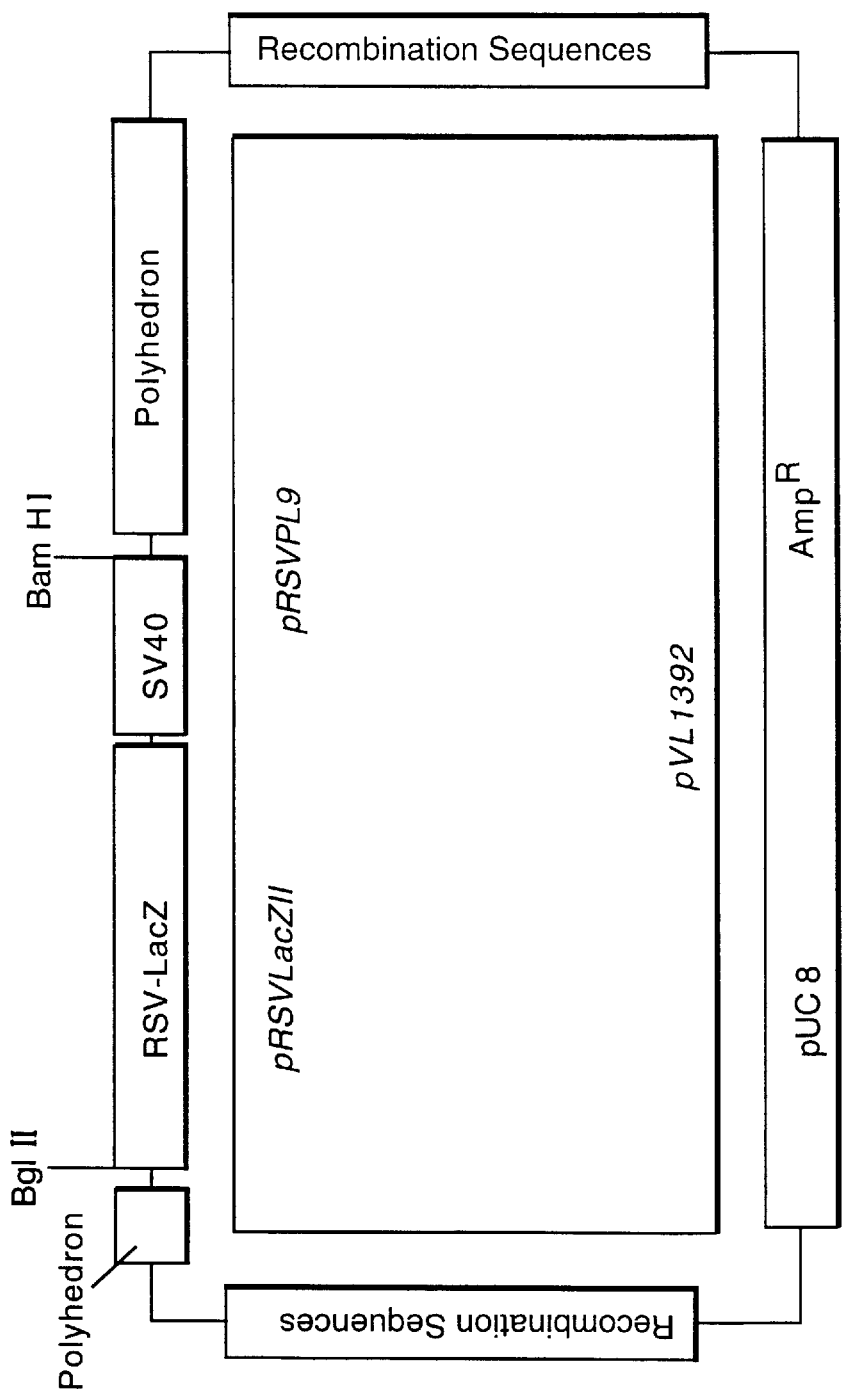

FIG. 1 is a schematic representation of the AcMNPV RSV-lacZ transfer plasmid, Z4.

Figure 2A:
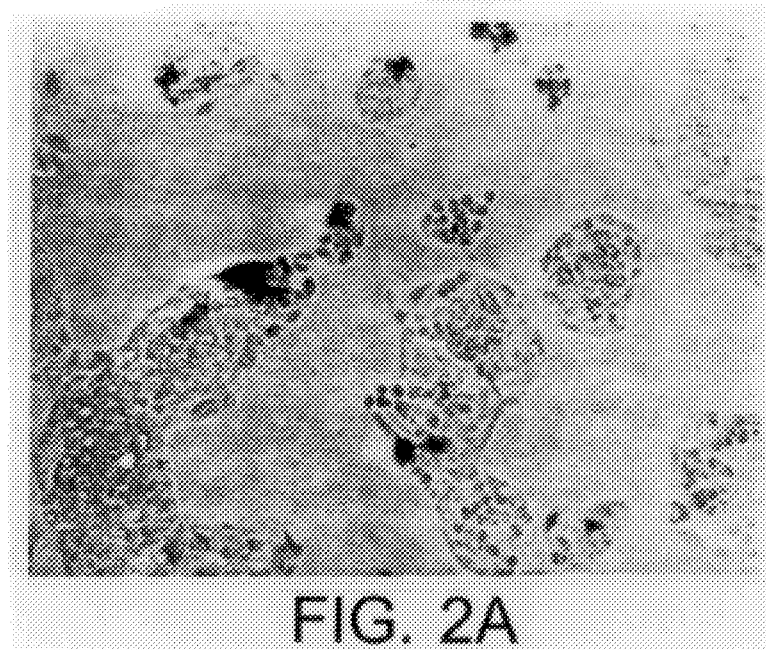
Figure 2B:
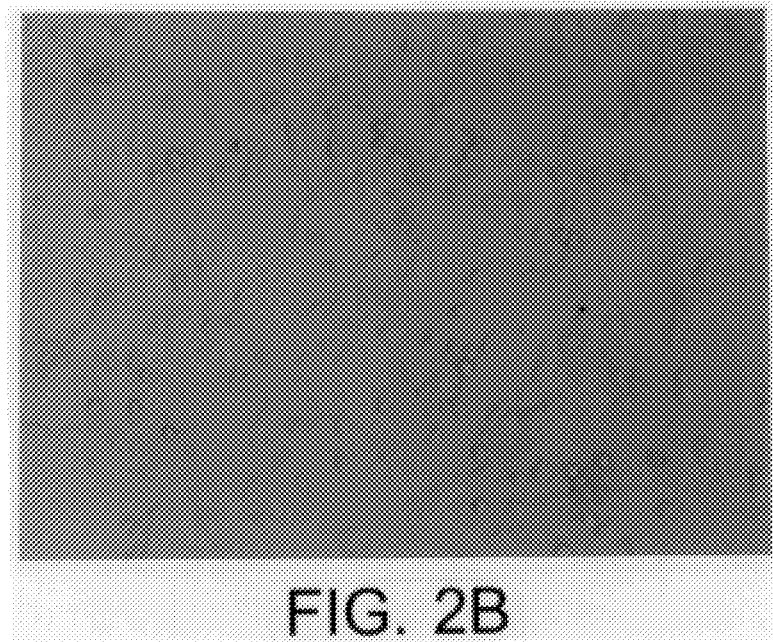
Figure 2C:
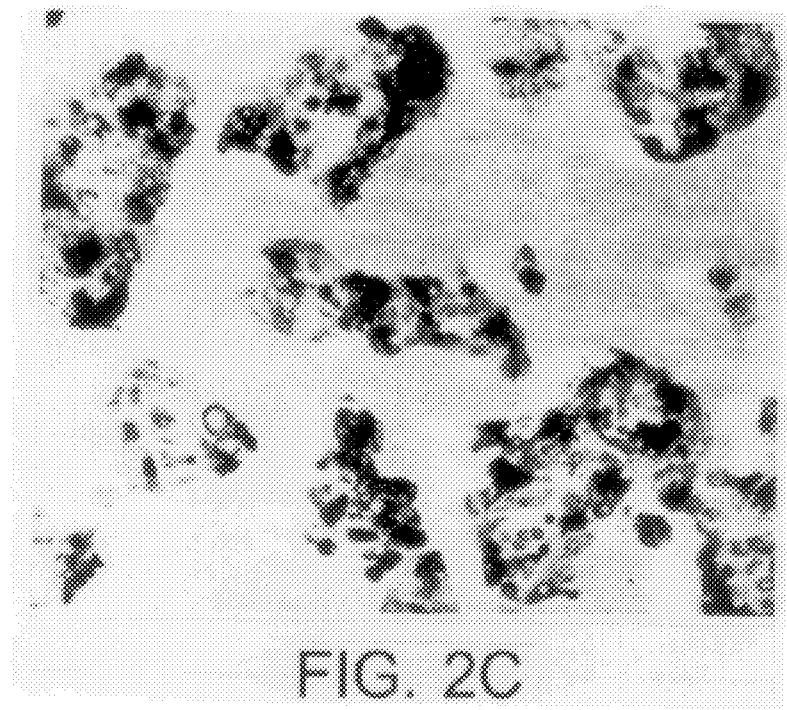
Figure 2D:
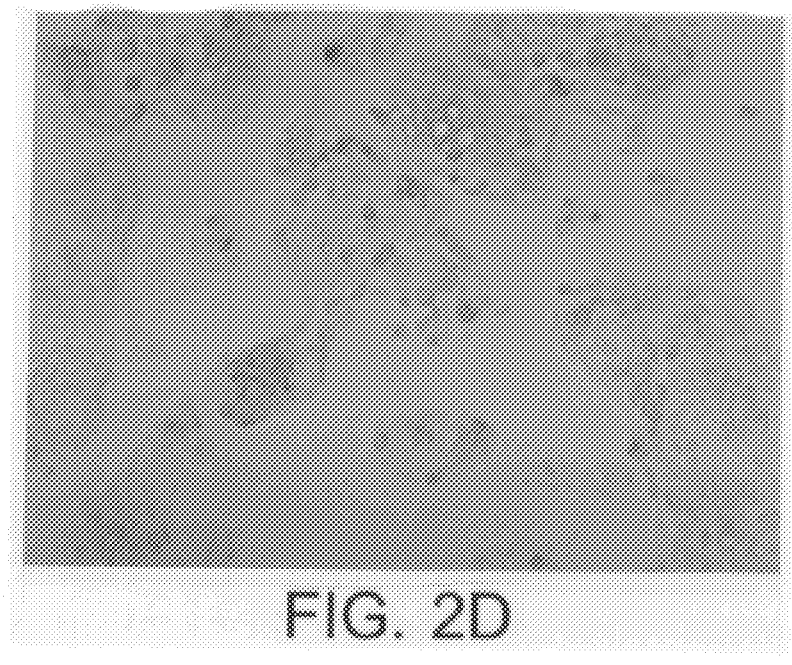

FIG. 2A is a photograph of HepG2 cells which were infected with AcMNPV carrying an RSV-lacZ cassette. FIG. 2B is a photograph of SKHep1 cells infected with AcMNPV carrying an RSV-lacZ cassette. FIG. 2C is a photograph of HepG2 cells infected with concentrated AcMNPV (having a titer of 7.8×10$^9$ pfu/ml) carrying an RSV-lacZ cassette. FIG. 2D is a photograph of HepG2 cells infected with AcMNPV carrying the lacZ gene operably linked to the polyhedron promoter.

EXAMPLE 1

Construction of a Baculovirus Carrying an Exogenous Gene

Genetic manipulation of a baculovirus can be accomplished with commonly-known recombination techniques for expressing proteins in baculovirus (O'Reilly et al., 1992, In: Baculovirus expression vectors, W. H. Freeman, New York). In this example, an AcMNPV was constructed by interrupting the polyhedron gene of the virus with a cassette which could direct the expression of a reporter gene. The reporter gene cassette included DNA sequences corresponding to the Rous Sarcoma Virus (RSV) promoter operably linked to the E. coli lacZ gene (FIG. 1). The reporter gene cassette also included sequences encoding Simian Virus 40 (SV40) RNA splicing and polyadenylation signals.

The RSV-lacZ AcMNPV transfer plasmid is named Z4 and was constructed as follows. An 847 bp fragment of pRSVPL9 including the SV40 RNA splicing signal and polyadenylation signal was excised using BglII and BamHI. pRSVPL9 was derived from pRSVglobin (Science 221: 551–553) by digesting pRSVglobin with BglII, adding a HindIII linker, and then cleaving the DNA with HindIII. A double-stranded polylinker made by hybridization of the oligonucleotides 5'AGCTGTCGACTCGAGGTACCA-GATCTCTAGA3' (SEQ ID NO:1) and 5'AGCTTCTA-GAGATCTGGTACCTCGAGTCGAC3' (SEQ ID NO:2) was ligated to the 4240 bp fragment having the RSV promoter and SV40 splicing and polyadenylation signals. The resulting plasmid has the polylinker in place of the globin sequences. The SV40 sequence of pRSVPL9 was cloned into the BamHI site of pVL1392 (Invitrogen and Pharmingen) using standard techniques. The resulting intermediate plasmid was named pVL/SV40. An RSV-lacZ cassette was excised from pRSVlacZII (Lin et al., 1991, Biotechniques 11: 344–348, and 350–351) with BglII and SpeI and inserted into the BglII and XbaI sites of pVL/SV40.

The AcMNPV RSV-lacZ virus, termed Z4, was prepared by homologous recombination of the Z4 transfer plasmid with linearized AcMNPV DNA. The AcMNPV virus used to prepare this DNA was ACV-EPA (Hartig et al., 1992, J. Virol. Methods 38: 61–70). The virus was plaque purified and amplified according to standard procedures (see, e.g., O'Reilly et al., infra). If desired, exogenous genes other than lacZ can be expressed from this construct, and promoters other than the RSV promoter can be used.

EXAMPLE 2

Infection of HepG2 Cells with Baculoviruses

I have discovered that AcMNPV is capable of expressing an exogenous gene in the human liver cell line HepG2. To demonstrate the efficacy of the AcMNPV expression system, I examined the ability of the AcMNPV RSV-lacZ virus to infect the the human hepatocyte line HepG2. One day prior to infection, the cell line (approximately 10$^6$ cells) was seeded in Eagles modifided MEM with 10% fetal calf serum in a 10 cm petri dish (for growth conditions, see the recommendations of the ATCC). On the day of infection, the media was removed and replaced with 2 ml of fresh media having 0.1 ml of unconcentrated or concentrated AcMNPV RSV-lacZ virus. As measured by plaque assay on Sf21 cells, the titer of the unconcentrated viral stock was 1.4×10$^8$ pfu/ml, and the titer of the concentrated viral stock was 7.8×10$^9$ pfu/ml. The concentrated viral stock was prepared by ultracentrifugation as previously described (O'Reilly et al., infra), and the virus stock was resuspended overnight in saline or phosphate-buffered saline (PBS) and filter-sterilized. The virus was allowed to adsorb onto the cells for 1–2 hours at 37° C. in 5% CO$_2$/95% air. The media containing the virus then was removed, and the cells were fed with 10 ml of fresh media. After 12–24 hours of post-infection incubation, the infected cells were assayed for β-galactosidase activity as follows. The cells were rinsed 3 times with PBS and then fixed for 5 minutes in PBS/2% paraformaldehyde/ 0.2% glutaraldehyde. The cells then were washed 3 times with PBS and then stained by incubation with a solution of PBS/ X-gal (0.5 mg/ml)/potassium ferrocyanide (35 mM)/ potassium ferricyanide (35 mM) for 1 to 12 hours at 37° C. The cells then were rinsed with PBS and photographed.

As shown in FIG. 2C, the AcMNPV RSV-lacZ virus infected the HepG2 cells and expressed β-galactosidase from the lacZ gene in over 25% of the HepG2 cells. FIG. 2C is a photograph of HepG2 cells infected with concentrated AcMNPV RSV-lacZ (virus having a titer of $7.8 \times 10^9$ pfu/ml). These data indicate that a baculovirus is capable of efficiently targeting expression of an exogenous gene to mammalian cells. The amount of β-galactosidase produced was linearly proportional to the amount of virus used in the infection over a wide range of multiplicities of infection. A multiplicity of infection of 15 pfu/cell (the titer was determined by plaque assay on Sf21 insect cells) resulted in expression of the lacZ gene in approximately 10% of the cells; a multiplicity of infection of 125 pfu/cell resulted in expression of lacZ in over 25% of the cells.

LacZ expression in HepG2 cells was monitored following infection with the AcMNPV RSV-lacZ virus. These data indicate that expression of lacZ declined with time, but lacZ-positive cells were detectable for at least 12 days following infection. To determine if expression of lacZ was the result of viral spread, culture supernatants taken 10 days after infection were titered on Sf21 cells by plaque assay. The HepG2 culture supernatants gave titers of less than 10 pfu/ml on Sf21 cells in plaque assays. These data indicate that there is little or no spread of AcMNPV after infection of HepG2 cells.

To confirm that lacZ expression in HepG2 cells resulted from transcription of the lacZ gene of the RSV-lacZ cassette and was not the result of lacZ enzyme carried within the AcMNPV virion, HepG2 cells were infected with an equivalent amount of the BacPAK6 virus, which expresses lacZ from the AcMNPV polyhedron promoter. While the BacPAK6 virus expressed very high levels of lacZ in insect cells, no lacZ expression was observed in HepG2 cells (FIG. 2D). Thus, these data indicate that the polyhedron transcription unit is not active in HepG2 cells, and no significant amount of lacZ enzyme is carried within the AcMNPV virion.

EXAMPLE 3

Use of a Baculovirus to Infect a Mammalian Cell

Now that I have demonstrated that a baculovirus can infect HepG2 cells and express an exogenous gene in those cells, other cells which can be infected by a baculovirus, including cells of tissues and organs, can easily be identified. The assay described above can be conveniently used to measure the ability of baculoviruses to direct expression of exogenous genes in other cells.

Nearly all mammalian cells are potential targets of the AcMNPV and other baculoviruses, and any cultured cell can be rapidly tested by substituting it for HepG2 in the assay described above. Candidate cell lines of particular interest include those which express a cell-surface asialoglycoprotein receptor (ASGP-R). HepG2 cells differ from SKHep1 human hepatocytes and 3T3 mouse fibroblast cells by the presence of ASGP-R on the cell surface. In my studies, β-galactosidase was expressed in fewer SKHep1 cells (FIG. 2B) or 3T3 cells than HepG2 cells. The lacZ gene was expressed in HepG2 cells at a frequency estimated as greater than 1,000 fold more than that in SKHep1 cells, based on quantitative counts of X-gal stained cells. Normal hepatocytes have 100,000 to 500,000 ASGP-R, each receptor internalizing up to 200 ligands per day. The ASGP-R may facilitate entry of the virus into the cell by providing a cell-surface receptor for glycoproteins on the virion. The glycosylation patterns of insect and mammalian cells differ, with the carbohydrate moieties on the surface of the virion having a decreased sialic acid content. Those carbohydrate moieties may mediate internalization and trafficking of the virion. In addition to the ASGP-R, other galactose-binding lectins exist in mammals (see, e.g., Jung et al., J. Biochem (Tokyo) 116:547–553) and can be used in the invention.

The coat protein of a virion which has been internalized by endocytosis undergoes a conformational change upon acidification of endosomes. Acidification allows the release of the nucleocapsid into the cytosol and transport of nucleocapsid to the nucleus. My data indicated that AcMNPV-mediated gene transfer of an RSV-lacZ gene cassette into HepG2 cells was inhibited by chloroquine, an agent which perturbs the pH of lysosomes, suggesting that the endocytic pathway can mediate gene transfer.

If desired, the ASGP-R can be expressed on the surface of a cell to be infected by the baculovirus. The genes encoding the ASGP-R have been cloned (Spiess et al., 1985, J. Biol. Chem. 260: 1979 and Spiess et al., 1985, PNAS 82: 6465), and standard retroviral, adeno-associated virus, or adenoviral vectors or chemical methods can be used for expression of the ASGP-R in the cell to be infected by a baculovirus. Expression of the ASGP-R in a cell may facilitate infection by the baculovirus. Other receptors for ligands on the virion, such as receptors for insect carbohydrates can also be expressed on the surface of the mammalian cell to be infected (see, e.g., Monsigny et al., 1979, Biol. Cellulaire 33: 289–300). Alternatively, the virion can be modified through chemical means (see, e.g., Neda, et al., 1991, J. Biol. Chem. 266: 14143–14146) or other methods, such as pseudotyping (see, e.g., Burns et al., 1993, PNAS 90: 8033–8037), to enable the virion to bind to other receptors on the mammalian cell. For example, viral coat proteins such as the *Vesicular stomatitis* virus G glycoprotein (VSV-G), or the influenza virus hemaglutinin protein can be used for pseudotyping. Alternatively, fusions between the baculovirus coat proteins (e.g., gp64) and a targeting molecule (e.g., VSV-G or VCAM) can be expressed on the virion. overexpression of a membrane protein, such as a cell adhesion molecule (e.g., VCAM), in insect packaging cells also can facilitate targeting of the virus to a mammalian cell. In addition, non-receptor-mediated events can mediate uptake of the baculovirus by the cell, leading to expression of an exogenous gene in the cell.

EXAMPLE 4

Therapeutic Use of a Baculovirus

The discovery that an AcMNPV efficiently expressed a lacZ reporter gene in the HepG2 cell line indicates that a baculovirus can be used therapeutically to express an exogenous gene in a cell of a mammal. For example, the method of the invention can facilitate expression of an exogenous gene in a cell of a patient for treatment of a disorder that is caused by a deficiency in gene expression. Numerous disorders are known to be caused by single gene defects (see Table 1), and many of the genes involved in gene deficiency disorders have been identified and cloned. Using the guidance of Examples 1–3, above, and standard cloning techniques (see, e.g., Ausubel et al., *Current Protocols in Molecular Biology*, John Wiley & Sons, (1989)), a baculovirus can be engineered to express a desired exogenous gene in a mammalian cell.

TABLE 1

Examples of Disorders Which Can be Treated with the Invention and Gene Products Which can be Manufactured with the Invention

| Gene Product | Disorder |
| --- | --- |
| fumarylacetoacetate hydrolase | hereditary tyrosinemia |
| phenylalanine hydroxylase | phenylketonuria |
| LDL receptor | familial hypercholesterolemia |
| alpha-1 antitrypsin | alpha-1 antitrypsin deficiency |
| glucose-6-phosphatase | glycogen storage diseases |
| porphobilinogen deaminase | diseases caused by errors in porphyrin metabolism, e.g., acute intermittent porphyria |
| CPS-I, OTC, AS, ASL, or arginase | disorders of the urea cycle |
| factors VIII & IX | hemophilia |
| cystathione β-synthase | homocystinuria |
| branched chain ketoacid decarboxylase | maple syrup urine disease |
| albumin | hypoalbuminemia |
| isovaleryl-CoA dehydrogenase | isovaleric acidemia |
| propionyl CoA carboxylase | propionic acidemia |
| methyl malonyl CoA mutase | methylmalonyl acidemia |
| glutaryl CoA dehydrogenase | glutaric acidemia |
| insulin | insulin-dependent diabetes |
| β-glucosidase | Gaucher's disease |
| pyruvate carboxylase | pyruvate carboxylase deficiency |
| hepatic phosphorylase or phosphorylase kinase | glycogen storage diseases |
| glycine decarboxylase, H-protein, or T-protein | non-ketotic hyperglycinemias |
| product of Wilson's disease gene pWD | Wilson's disease |
| Menkes disease protein | Menkes disease |

The invention can also be used to facilitate the expression of a desired gene in a cell having no obvious deficiency. For example, the invention can be used to express insulin in a hepatocyte of a patient in order to supply the patient with insulin in the body. Other examples of proteins which can be expressed in the liver for delivery into the system circulation of the mammal include hormones, growth factors, and interferons. The invention can also be used to express a regulatory gene or a gene encoding a transcription factor (e.g., a VP16-tet repressor gene fusion) in a cell to control the expression of another gene (e.g., genes which are operably-linked to a tet operator sequence; see, e.g., Gossen et al., 1992, PNAS 89: 5547–5551). If desired, tumor suppressor genes such as the gene encoding p53 can be expressed in a cell in a method of treating cancer. Other useful gene products include RNA molecules for use in RNA decoy, antisense, or ribozyme-based methods of inhibiting gene expression (see, e.g., Yu et al., 1994, Gene Therapy 1: 13–26). If desired, the invention can be used to express a gene, such as cytosine deaminase, whose product will alter the activity of a drug or prodrug, such as 5-fluorocytosine, in a cell (see, e.g., Harris et al., 1994, Gene Therapy 1: 170–175). Methods such as the use of ribozymes, antisense RNAs, transdominant repressors, polymerase mutants, or core or surface antigen mutants can be used to suppress hepatitis viruses (e.g., hepatitis virus A, B, C, or D) in a cell. Other disorders such as familial hemachromatosis can also be treated with the invention.

Preferred genes for expression include those genes which encode proteins that are expressed in normal hepatocytes. For example, genes encoding enzymes involved in the urea cycle, such as the genes encoding carbamoyl phosphate synthetase (CPS-I), ornithine transcarbamylase (OTC), arginosuccinate synthetase (AS), arginosuccinate lyase (ASL), and arginase are useful in this method. All of these genes have been cloned (for OTC, see Horwich et al., 1984, Science 224:1068–1074 and Hata et al., 1988, J. Biochem (Tokyo) 103:302–308; for AS, see Bock et al., 1983, Nucl. Acids Res. 11: 6505; Surh et al., 1988, Nucl. Acids Res. 16: 9252; and Dennis et al., 1989, PNAS 86: 7947; for ASL, see O'Brien et al., 1986, PNAS 83: 7211; for CPS-I, see Adcock et al., 1984, (Abstract) Fed. Proc. 43: 1726; for arginase, see Haraguchi et al., PNAS 84: 412). Subcloning these genes into a baculovirus can be readily accomplished with common techniques.

The baculovirus can be formulated into pharmaceutical compositions by admixture with pharmaceutically acceptable non-toxic excipients and carriers (e.g., saline) for administration to a mammal. In practicing the invention, the baculovirus can be prepared for use in parenteral administration (e.g., for intravenous injection, intra-arterial injection, intraperitoneal injection, intrathecal injection, direct injection into an area (e.g., intramuscular injection), particularly in the form of liquid solutions or suspensions. The baculovirus can also be prepared for intranasal or intrabronchial administration, particularly in the form of nasal drops or aerosols.

In another method of practicing the invention, the baculovirus is used to infect a cell outside of the mammal to be treated (e.g., a cell in a donor mammal or a cell in vitro), and the infected cell then is administered to the mammal to be treated. In this method, the cell can be autologous or heterologous to the mammal to be treated. For example, an autologous hepatocyte obtained in a liver biopsy can be used. The cell is cultured and infected with the baculovirus using the guidance provided herein in combination with what is known in the art (see, e.g., Grossman et al., 1994, Nature Genetics 6: 335). The cell can then be administered to the patient by injection (e.g., into the peritoneal cavity or by intravenous injection). In this method, a volume of hepatocytes totaling about 1%–10% of the volume of the entire liver can be used.

The amount of baculovirus or number of infected cells to be administered to a mammal and the frequency of administration are dependent upon a variety of factors such as the sensitivity of methods for detecting expression of the exogenous gene, the strength of the promoter used, the severity of the disorder to be treated, and the target cell(s) of the virus. Generally, the virus is administered at a multiplicity of infection of about 0.1–1,000; preferably, the multiplicity of infection is about 5–100; more preferably, the multiplicity of infection is about 10–50.

Delivery of a baculovirus to a cell and expression of the exogenous gene can be monitored using standard techniques for assaying gene expression. For example, delivery of AcMNPV to hepatocytes in vivo can be detected by obtaining cells in a liver biopsy performed using standard techniques and detecting AcMNPV DNA or RNA (with or without amplification by PCR) by common procedures such as Southern or Northern blotting, slot or dot blotting, or in situ hybridization. Suitable probes which hybridize to nucleic acids of AcMNPV, the promoter, or the exogenous gene can be conveniently prepared by one skilled in the art of molecular biology.

Expression of an exogenous gene in a cell of a mammal can be followed by assaying a cell or fluid (e.g., serum) obtained from the mammal for RNA or protein corresponding to the gene. Detection techniques commonly used by molecular biologists (e.g., Northern or Western blotting, in situ hybridization, slot or dot blotting, PCR amplification, SDS-PAGE, immunostaining, RIA, and ELISA) can be used to measure gene expression. If desired, the lacZ reporter gene can be used to measure the ability of a particular baculovirus to target gene expression to certain tissues or cells. Examination of tissue can involve: (a) snap-freezing the tissue in isopentane chilled with liquid nitrogen; (b) mounting the tissue on cork using O.C.T. and freezing; (c) cutting the tissue on a cryostat into 10 μm sections; (d) drying the sections and treating them with paraformaldehyde; (e) staining the tissue with X-gal (0.5 mg/ml)/ferrocyanide (35 mM)/ferricyanide (35 mM) in PBS; and (f) analyzing the tissue by microscopy.

The therapeutic effectiveness of expressing an exogenous gene in a cell can be assessed by monitoring the patient for known signs or symptoms of a disorder. For example, amelioration of OTC deficiency and CPS deficiency can be detected by monitoring plasma levels of ammonium or orotic acid. Similarly, plasma citrulline levels provide an indication of AS deficiency, and ASL deficiency can be followed by monitoring plasma levels of arginosuccinate. Parameters for assessing treatment methods are known to those skilled in the art of medicine (see, e.g., Maestri et al., 1991, J. Pediatrics, 119: 923–928).

OTHER EMBODIMENTS

Baculoviruses other than *Autographa californica* can be used in the invention. For example, *Bombyx mori* nuclear polyhedrosis virus, *Orgyia pseudotsugata* mononuclear polyhedrosis virus, *Trichoplusia ni* mononuclear polyhedrosis virus, *Heliothhis zea* baculovirus, *Lymantria dispar* baculovirus, *Cryptophlebia leucotreta* granulosis virus, *Penaeus monodon*-type baculovirus, *Plodia interpunctella* granulosis virus, *Mamestra brassicae* nuclear polyhedrosis virus, and *Buzura suppressaria* nuclear polyhedrosis virus can be used. Promoters other than the RSV LTR can be used; for example the SV40 early promoter, the CMV IE promoter, the adenovirus major late promoter, and the Hepatitis B promoter can be used. In addition, promoters which are cell-type-specific, stage-specific, or tissue-specific can be used. For example, several liver-specific promoters, such as the albumin promoter/enhancer, have been described (see, e.g., Shen et al., 1989, DNA 8: 101–108; Tan et al., 1991, Dev. Biol. 146: 24–37; McGrane et al., 1992, TIBS 17: 40–44; Jones et al., J. Biol. Chem. 265: 14684–14690; and Shimada et al., 1991, Febs Letters 279: 198–200).

If desired, the baculovirus genome can be engineered to carry a human origin of replication; such sequences have been identified (Burhans et al., 1994, Science 263: 639–640) and can facilitate replication in human cells. Other origins of replication, such as the Epstein-Barr Virus replication origin and trans-acting factor, can facilitate gene expression in human cells. Optionally, the baculovirus can be engineered to express more than one exogenous gene (e.g., the virus can be engineered to express OTC and AS). If desired, the virus can be engineered to facilitate targeting of the virus to certain cell types. For example, ligands which bind to cell surface receptors other than the ASGP-R can be expressed on the surface of the virion. Alternatively, the virus can be chemically modified to target the virus to a particular receptor.

If desired, the cell to be infected can first be stimulated to be mitotically active. In culture, agents such as chloroform can be used to this effect; in vivo, stimulation of liver cell division, for example, can be induced by partial hepatectomy (see, e.g., Wilson, et al., 1992, J. Biol. Chem. 267: 11283–11489). Optionally, the baculovirus genome can be engineered to carry a herpes simplex virus thymidine kinase gene; this would allow cells harboring the baculovirus genome to be killed by gancicylovir. If desired, the baculovirus could be engineered such that it is defective in growing on insect cells. Such a strain of baculovirus could provide added safety and would be propagated on a complementing packaging line. An example of a defective baculovirus is one in which an immediate early gene, such as IE1, has been deleted. This deletion can be made by targeted recombination in yeast, and the defective virus can be replicated in insect cells in which the IE1 gene product is supplied in trans. If desired, the baculovirus can be treated with neuraminidase to reveal additional terminal galactose residues prior to infection (see, e.g., Morell et al., 1971, J. Biol. Chem. 246: 1461–1467).

What is claimed is:

1. A method of expressing an exogenous gene in a mammalian cell in vitro, said method comprising:
   a) introducing into the cell a baculovirus whose genome comprises said exogenous gene; and
   b) allowing said cell to live under conditions such that said exogenous gene is expressed.

2. The method of claim 1, wherein said baculovirus is a nuclear polyhedrosis virus.

3. The method of claim 2, wherein said baculovirus is an *Autographa californica* virus.

4. The method of claim 3, wherein said genome lacks a functional polyhedron gene.

5. The method of claim 1, wherein said genome further comprises a promoter of a long-terminal repeat of a transposable element.

6. The method of claim 1, wherein said genome further comprises a promoter of a long-terminal repeat of a retrovirus.

7. The method of claim 6, wherein said retrovirus is Rous Sarcoma Virus.

8. The method of claim 1, wherein said genome further comprises a polyadenylation signal and an RNA splicing signal.

9. The method of claim 1, wherein said genome further comprises a cell-type-specific promoter.

10. The method of claim 1, wherein said cell is a hepatocyte.

11. The method of claim 1, wherein said cell is a human cell.

12. The method of claim 1, wherein said cell comprises an asialoglycoprotein receptor.

13. The method of claim 1, wherein said gene encodes carbamoyl synthetase I.

14. The method of claim 1, wherein said gene encodes ornithine transcarbamylase.

15. The method of claim 1, wherein said gene encodes arginosuccinate synthetase.

16. The method of claim 1, wherein said gene encodes arginosuccinate lyase.

17. The method of claim 1, wherein said gene encodes arginase.

18. The method of claim 1, wherein said gene encodes a gene product selected from the group consisting of fumarylacetoacetate hydrolase, phenylalanine hydroxylase, alpha-1 antitrypsin, glucose-6-phosphatase, low-density-lipoprotein receptor, and porphobilinogen deaminase, factor VIII, factor IX, cystathione β-synthase, branched chain ketoacid decarboxylase, albumin, isovaleryl-CoA dehydrogenase, propionyl CoA carboxylase, methyl malonyl CoA mutase, glutaryl CoA dehydrogenase, insulin, β-glucosidase, pyruvate carboxylase, hepatic phosphorylase, phosphorylase kinase, glycine decarboxylase, H-protein, T-protein, Menkes disease protein, and the product of Wilson's disease gene pWD.

19. The method of claim 1, wherein said baculovirus is introduced into said cell in vitro.

20. A nucleic acid comprising:
   a baculovirus genome;
   an exogenous mammalian gene; and
   an exogenous promoter selected from the group consisting of a mammalian promoter and a Hepatitis B viral promoter, wherein said gene is operably linked to said promoter.

21. The nucleic acid of claim 20, wherein said promoter is selected from the group consisting of cell-type-specific promoters, tissue-specific promoters, inducible promoters, and stage-specific promoters.

22. The nucleic acid of claim 21, wherein said promoter is a liver-specific promoter.

23. The nucleic acid of claim 20, wherein said gene encodes a human gene product.

24. The nucleic acid of claim 20, wherein said gene encodes a therapeutic gene product.

25. The nucleic acid of claim 20, wherein said gene encodes a gene product selected from the group consisting of carbamoyl synthetase I, ornithine transcarbamylase, arginosuccinate synthetase, arginosuccinate lyase, arginase fumarylacetoacetate hydrolase, phenylalanine hydroxylase, alpha-1 antitrypsin, glucose-6-phosphatase, low-density-lipoprotein receptor, porphobilinogen deaminase, arginase, factor VIII, factor IX, cystathione β-synthase, branched chain ketoacid decarboxylase, albumin, isovaleryl-CoA dehydrogenase, propionyl CoA carboxylase, methyl malonyl CoA mutase, glutaryl CoA dehydrogenase, insulin, β-glucosidase, and pyruvate carboxylase, hepatic phosphorylase, phosphorylase kinase, glycine decarboxylase, H-protein, T-protein, Menkes disease protein, the product of Wilson's disease gene pWD, growth factors, interferons, cytosine deaminase, and a herpes simplex virus thymidine kinase gene.

26. A cell, in vitro that contains a nucleic acid, wherein said nucleic acid comprises:
   a baculovirus genome;
   an exogenous mammalian gene; and
   an exogenous promoter selected from the group consisting of a mammalian promoter and a Hepatitis B viral promoter, wherein said gene is operably linked to said promoter.

27. The cell of claim 26, wherein said cell is a mammalian cell.

28. The cell of claim 26, wherein said promoter is selected from the group consisting of cell-type-specific promoters, tissue-specific promoters, stage-specific promoters, and inducible promoters.

29. The cell of claim 28, wherein said promoter is a liver-specific promoter.

30. The cell of claim 26, wherein said gene encodes a human gene product.

31. The cell of claim 26, wherein said gene encodes a therapeutic gene product.

32. The cell of claim 26, wherein said gene encodes a gene product selected from the group consisting of carbamoyl synthetase I, ornithine transcarbamylase, arginosuccinate synthetase, arginosuccinate lyase, arginase fumarylacetoacetate hydrolase, phenylalanine hydroxylase, alpha-1 antitrypsin, glucose-6-phosphatase, low-density-lipoprotein receptor, porphobilinogen deaminase, arginase, factor VIII, factor IX, cystathione β-synthase, branched chain ketoacid decarboxylase, albumin, isovaleryl-CoA dehydrogenase, propionyl CoA carboxylase, methyl malonyl CoA mutase, glutaryl CoA dehydrogenase, insulin, β-glucosidase, and pyruvate carboxylase, hepatic phosphorylase, phosphorylase kinase, glycine decarboxylase, H-protein, T-protein, Menkes disease protein, the product of Wilson's disease gene pWD, growth factors, interferons, cytosine deaminase, and a herpes simplex virus thymidine kinase gene.

33. The nucleic acid of claim 20, wherein said baculovirus genome lacks an immediate early gene.

34. The cell of claim 26, wherein said baculovirus genome lacks an immediate early gene.

35. The nucleic acid of claim 20, wherein said baculovirus genome lacks a functional polyhedron gene.

36. The cell of claim 26, wherein said baculovirus lacks a functional polyhedron gene.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:1:

AGCTGTCGAC TCGAGGTACC AGATCTCTAG A                    3 1

( 2 ) INFORMATION FOR SEQ ID NO:2:

( i ) SEQUENCE CHARACTERISTICS:
  ( A ) LENGTH: 31 base pairs
  ( B ) TYPE: nucleic acid
  ( C ) STRANDEDNESS: single
  ( D ) TOPOLOGY: linear ( i i ) MOLECULE TYPE: DNA ( x i ) SEQUENCE DESCRIPTION: SEQ ID NO:2:

AGCTTCTAGA GATCTGGTAC CTCGAGTCGA C    31